(12) United States Patent
Keidar et al.

(10) Patent No.: US 7,306,593 B2
(45) Date of Patent: Dec. 11, 2007

(54) PREDICTION AND ASSESSMENT OF ABLATION OF CARDIAC TISSUE

(75) Inventors: Yaron Keidar, Haifa (IL); Assaf Govari, Haifa (IL); Yitzhack Schwartz, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 247 days.

(21) Appl. No.: 10/757,288

(22) Filed: Jan. 14, 2004

(65) Prior Publication Data

US 2004/0147920 A1    Jul. 29, 2004

Related U.S. Application Data

(63) Continuation-in-part of application No. 10/277,079, filed on Oct. 21, 2002, now Pat. No. 7,001,383.

(51) Int. Cl.
*A61B 18/18* (2006.01)

(52) U.S. Cl. .......................... 606/34; 606/41

(58) Field of Classification Search ............ 606/31–35, 606/41, 48–50; 607/101, 102, 116, 122; 600/437, 439, 459, 461
See application file for complete search history.

(56) References Cited

U.S. PATENT DOCUMENTS

| | | | |
|---|---|---|---|
| 5,546,940 A * | 8/1996 | Panescu et al. ............. | 600/374 |
| 5,546,951 A | 8/1996 | Ben-Haim | |
| 5,588,432 A | 12/1996 | Crowley | |
| 5,657,755 A * | 8/1997 | Desai ......................... | 600/374 |
| 5,964,753 A | 10/1999 | Edwards | |
| 6,014,579 A | 1/2000 | Pomeranz et al. | |
| 6,027,500 A | 2/2000 | Buckles et al. | |
| 6,052,618 A | 4/2000 | Dahlke et al. | |
| 6,067,371 A | 5/2000 | Gouge | |
| 6,070,094 A | 5/2000 | Swanson et al. | |

(Continued)

FOREIGN PATENT DOCUMENTS

EP       1 182 619 A2     2/2002

(Continued)

OTHER PUBLICATIONS

European Search Report EP 03256602 dated Sep. 8, 2004.

(Continued)

*Primary Examiner*—Michael Peffley
(74) *Attorney, Agent, or Firm*—Louis J. Capezzuto

(57) ABSTRACT

A method for ablating tissue in an organ inside a body of a subject includes bringing a probe inside the body into a position in contact with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

21 Claims, 5 Drawing Sheets

U.S. PATENT DOCUMENTS

| | | | |
|---|---|---|---|
| 6,095,150 | A | 8/2000 | Panescu et al. |
| 6,179,833 | B1 | 1/2001 | Taylor |
| 6,322,558 | B1 | 11/2001 | Taylor et al. |
| 6,506,189 | B1 * | 1/2003 | Rittman et al. ............... 606/41 |
| 6,575,969 | B1 * | 6/2003 | Rittman et al. ............... 606/41 |
| 6,690,963 | B2 * | 2/2004 | Ben-Haim et al. .......... 600/424 |
| 2003/0078494 | A1 | 4/2003 | Panescu et al. |
| 2003/0109871 | A1 * | 6/2003 | Johnson et al. ............... 606/42 |

FOREIGN PATENT DOCUMENTS

WO       WO 96/32885 A1    10/1996

OTHER PUBLICATIONS

European Search Report EP 05250156 dated May 13, 2005.

Germain D. et al: "MR Monitoring of Laser-Induced Lesions of the Liver in Vivo in a Low-Field Open Magnet Temperature Mapping and Lesion Size Prediction"; Journal of Magnetic Resonance Imaging; Jan. 2001; pp. 42-49; vol. 13; Wiley-Liss, Inc.

Hong Cao et al: "Using Electrical Impedance to Predict Catheter-Endocardial Contact During RF Cardiac Ablation"; IEEE Transactions on Biomedical Engineering; Mar. 2002; pp. 247-253; vol. 49, No. 3; IEEE.

* cited by examiner

PREDICTION AND ASSESSMENT OF ABLATION OF CARDIAC TISSUE

CROSS-REFERENCE TO RELATED APPLICATION

This application is a continuation-in-part of U.S. patent application No. 10/277,079, filed Oct. 21, 2002, now U.S. Pat. No. 7,001,383 which is assigned to the assignee of the present patent application and whose disclosure is incorporated herein by reference.

FIELD OF THE INVENTION

The present invention relates generally to minimally-invasive treatment of organs inside the body, and specifically to methods and devices for prediction and assessment of ablation treatments applied to cardiac tissue.

BACKGROUND OF THE INVENTION

Radio frequency (RF) ablation is widely used for treating cardiac arrhythmias. RF ablation is commonly carried out by inserting a catheter through the patient's vascular system into the heart, and bringing the distal tip of the catheter into contact with the cardiac tissue at the site that is to be ablated. RF electrical current is then conducted through wires in the catheter to one or more electrodes at the tip of the catheter, which apply the RF energy to the myocardium. The RF energy is absorbed in the tissue, heating it to the point (typically about 50° C.) at which it permanently loses its electrical excitability. When this sort of procedure is successful, it creates non-conducting lesions in the cardiac tissue, which disrupt the abnormal electrical pathway causing the arrhythmia.

It is often difficult to determine the proper dosage of RF energy that should be applied in an ablation procedure in order to achieve the desired result. When the dosage is insufficient, the non-conducting lesion will not extend deeply enough through the heart wall to disrupt the abnormal conduction, so that arrhythmia may persist or return after the procedure is completed. On the other hand, excessive RF dosage may cause dangerous damage to the tissue at and around the ablation site. The proper RF dosage is known to vary from case to case depending on various factors, such as catheter geometry, thickness of the heart wall, quality of the electrical contact between the catheter electrode and the heart wall, and blood flow in the vicinity of the ablation site (which carries away heat generated by the RF energy).

In order to improve the precision and consistency of RF ablation procedures, attempts have been made to predict and control the ablation based on measurement of physiological parameters of relevance. One parameter that has been found useful in this context is the electrical impedance between the catheter electrode and the endocardial tissue, as described, for example, by Cao et al., in "Using Electrical Impedance to Predict Catheter-Endocardial Contact During RF Cardiac Ablation," *IEEE Transactions on Biomedical Engineering* 49:3 (2002), pages 247-253, which is incorporated herein by reference. The authors note that the electrode-endocardial contact includes two aspects: the depth to which the catheter is inserted into the myocardium and the angle between the catheter and the endocardial surface. These qualities, however, are difficult to ascertain in catheterization systems known in the art, and they may vary during the ablation procedure. The article describes a method for predicting the insertion depth of the catheter using electrical impedance measurements. The use of impedance measurements in controlling RF ablation is also described in U.S. Pat. No. 6,391,024, whose disclosure is incorporated herein by reference.

Various other methods and devices are known in the art for controlling ablation based on physiological measurement. For example, U.S. Patent Application Publication US 2002/0169445 A1, whose disclosure is incorporated herein by reference, describes a RF ablation system in which energy delivery is linked to fluid flow. Fluid flow rate in a biological organ is provided by an ECG device or a flow sensor. A processor assesses whether the flow rate is low or high, and controls the RF generator accordingly. As another example, U.S. Patent Application Publication US 2002/0128639 A1, whose disclosure is also incorporated herein by reference, describes a device and method for forming a lesion, wherein the temperature response of the tissue to be ablated (in this case by focused ultrasound) is measured in advance of the ablation. The temperature response is affected by factors such as tissue thickness, amount of fat and muscle, and blood flow through and around the region in question. The temperature response of the tissue is analyzed to determine the appropriate ablation technique.

The catheter that is used to perform the RF ablation may also be used to observe the results of the ablation. For example, U.S. Pat. No. 5,588,432, whose disclosure is incorporated herein by reference, describes catheters for imaging, sensing electrical potentials and ablating tissue. In one embodiment described in the patent, a sonolucent electrode at the tip of the catheter is used to perform RF ablation. An ultrasonic transducer is positioned to transmit ultrasonic signals through the electrode into the heart tissue, in order to create an ultrasonic image. The imaging capability of the catheter can be used to determine immediately whether a specific change to the tissue has resulted from the ablation. Desiccation of tissue manifests itself as a brightening of the region of the ultrasound image corresponding to the location of the lesion. This brightening corresponds to increased reflection of ultrasonic signals.

SUMMARY OF THE INVENTION

Embodiments of the present invention provide methods and apparatus for use in ablating body tissue, and particularly heart tissue. These embodiments are based on a probe, such as a catheter, having an ablation electrode at its tip, and comprising a position and orientation sensor. The sensor is used to continuously measure the position and orientation of the probe, and thus provides an accurate measurement of the angle and penetration depth of the probe tip relative to the tissue that is to be ablated.

The measured angle and penetration depth are used in predicting the extent of ablation of the tissue that expected for a given dosage of radiation applied by the catheter in this position. Because the probe permits the angle and penetration depth to be measured directly, rather than relying on secondary indicators such as impedance, it enables more accurate prediction of the extent of the ablation region than is possible in systems known in the art. Optionally, the probe may be configured to make other relevant measurements, such as impedance, temperature, tissue characteristics and flow, in order to refine the prediction.

In some embodiments of the present invention, the probe comprises a cardiac catheter, which is employed, prior to ablating the tissue, to create a map of the interior of the heart, as described in the above-mentioned parent application (U.S. Ser. No. 10/277,079). The position sensor readings are then used to determine the position and orientation of the catheter relative to the tissue on the basis of this map. The predicted extent of ablation is displayed on a graphical representation of the map, so that the operator of the catheter can visualize the region that will be ablated and can adjust the RF dosage up or down to enlarge or reduce the region.

After applying the selected dosage, the catheter is used to measure the actual extent of the ablation, using ultrasonic imaging, for example. The actual, measured extent of the ablation is displayed on the map, typically superimposed for comparison on the predicted extent of ablation. The operator can use this visual comparison to plan and adjust the RF dosage that will be administered in subsequent ablation steps at the same site or other sites in the heart. Additionally or alternatively, the catheter console, which performs the above-mentioned mapping and prediction functions, may use the comparison of predicted and actual results to adaptively improve the accuracy of prediction in subsequent ablation steps.

There is therefore provided, in accordance with an embodiment of the present invention, a method for ablating tissue in an organ inside a body of a subject, including:

bringing a probe inside the body into a position in contact with the tissue to be ablated;

measuring one or more local parameters at the position using the probe prior to ablating the tissue;

displaying a map of the organ showing, based on the one or more local parameters, a predicted extent of ablation of the tissue to be achieved for a given dosage of energy applied at the position using the probe;

applying the given dosage of energy to ablate the tissue using the probe;

measuring an actual extent of the ablation at the position using the probe subsequent to ablating the tissue; and displaying the measured actual extent of the ablation on the map for comparison with the predicted extent.

In disclosed embodiments, bringing the probe into the position includes using a position sensor in the probe to determine coordinates of the probe at the position in which the probe is in contact with the tissue. Typically, measuring the one or more local parameters includes measuring at least one of a penetration depth of the probe in the tissue and an orientation angle of the probe relative to the tissue, using the position sensor. Additionally or alternatively, displaying the map includes bringing the probe into contact with the tissue at multiple positions inside the organ, and recording the coordinates of the probe at the multiple positions in order to generate the map. Displaying the map may further include measuring electrical potentials at the multiple positions, and showing an indication of electrical activity on the map, based on the measured electrical potentials.

In some embodiments, measuring the one or more local parameters includes sensing ultrasonic waves reflected from the tissue using one or more transducers in the probe. In one embodiment, sensing the ultrasonic waves includes assessing a propagation speed of the ultrasonic waves in the tissue, so as to estimate a temperature of the tissue. In another embodiment, sensing the ultrasonic waves includes assessing blood flow responsively to the reflected ultrasonic waves. Typically, measuring the actual extent of the ablation includes sensing the ultrasonic waves reflected from the tissue using the one or more transducers after applying the given dosage of the energy.

In a disclosed embodiment, measuring the one or more local parameters includes measuring an orientation angle of the probe relative to the tissue, and displaying the map includes predicting the extent of the ablation responsively to the orientation angle.

Typically, measuring the one or more local parameters includes measuring at least one local parameter selected from a list of the local parameters consisting of a penetration depth of the probe in the tissue, an electrical impedance between the probe and the tissue, a temperature of the tissue and a flow of blood associated with the tissue, and displaying the map includes predicting the extent of the ablation responsively to the at least one factor.

The method may also include adjusting the dosage of the energy responsively to the map.

In a disclosed embodiment, applying the given dosage includes transmitting radio frequency (RF) energy into the tissue through an electrode fixed to the probe.

In a further embodiment, applying the given dosage includes ablating a succession of mutually-adjacent sites in the tissue, and displaying the measured actual extent of the ablation includes providing a visual indication of overlap between the sites.

In some embodiments, the organ includes a heart, and wherein the probe includes a catheter.

There is also provided, in accordance with an embodiment of the present invention, a method for ablating tissue in an organ inside a body of a subject, including:

bringing a probe inside the body into contact with the tissue to be ablated;

measuring a position and orientation of the probe relative to the tissue with which the probe is in contact;

predicting an extent of ablation of the tissue to be achieved for a given dosage of energy applied by the probe, responsively to the measured position and orientation; and applying the given dosage of energy to ablate the tissue using the probe.

In disclosed embodiments, measuring the position and orientation includes determining location and orientation coordinates of the probe using a position sensor in the probe. Typically, the position sensor includes one or more sensor coils, and determining the coordinates includes sensing an externally-applied magnetic field using the sensor coils in order to determine the coordinates. Additionally or alternatively, measuring the position and orientation includes bringing the probe into contact with the tissue at multiple positions inside the organ, and recording the coordinates of the probe at the multiple positions in order to generate a map of the organ, and determining the orientation angle of the probe relative to the tissue using the map. Determining the position and orientation may further include determining a depth of penetration of the probe into the tissue, based on the coordinates of the probe and on the map, wherein predicting the extent of the ablation includes estimating the predicted extent of the ablation responsively to the depth of penetration and the orientation angle of the probe.

There is additionally provided, in accordance with an embodiment of the present invention, apparatus for ablating tissue in an organ in a body of a subject, including:

a probe, which is adapted to be inserted into the body so as to contact the tissue to be ablated at a desired position in the organ, the probe including:

at least one sensor, which is adapted to measure one or more local parameters at the position prior to and after ablating the tissue; and an ablation device, which is adapted to apply a given dosage of energy to the tissue so as to ablate the tissue;

a display, which is adapted to display a map of the organ; and a controller, which is adapted to generate the map showing, based on the one or more local parameters measured by the at least one sensor, a predicted extent of ablation of the tissue to be achieved for the given dosage of energy, and an actual extent of the ablation determined subsequent to ablating the tissue, for comparison with the predicted extent.

There is further provided, in accordance with an embodiment of the present invention, apparatus for ablating tissue in an organ inside a body of a subject, including:

a probe, which is adapted to be inserted into the body so as to contact the tissue to be ablated, the probe including:

a position sensor, which is adapted to generate an output indicative of a position and orientation of the probe relative to the tissue with which the probe is in contact; and an ablation device, which is adapted to apply a given dosage of energy to the tissue so as to ablate the tissue;

a display, which is adapted to display a map of the organ; and a controller, which is adapted to compute, based on the position and orientation of the probe, a prediction of an extent of ablation of the tissue to be achieved for the given dosage of energy, so as to enable the dosage to be adjusted responsively to the prediction.

The present invention will be more fully understood from the following detailed description of the embodiments thereof, taken together with the drawings in which:

DETAILED DESCRIPTION OF EMBODIMENTS

Figure 1:
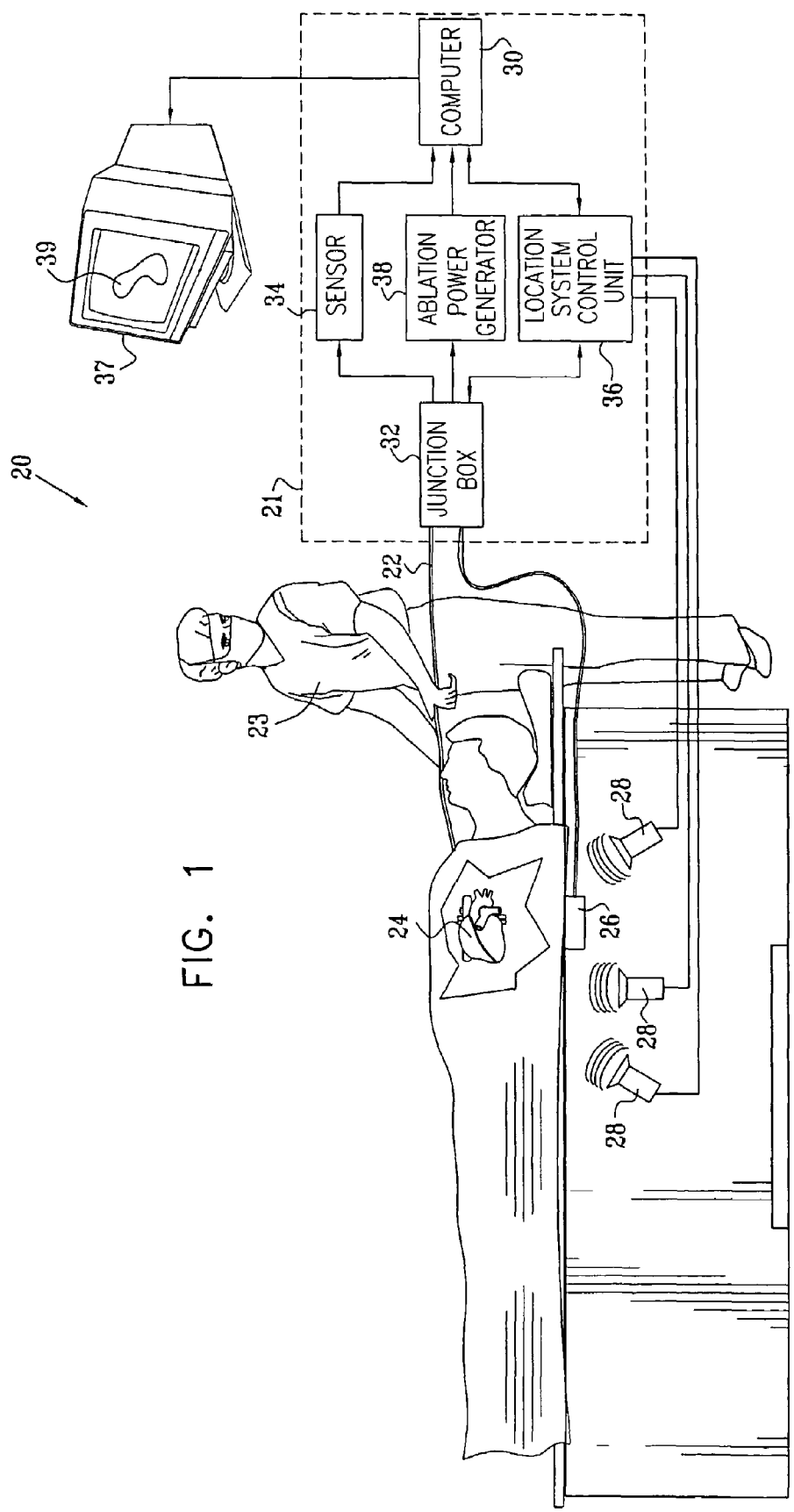
FIG. 1 is a schematic, pictorial illustration of a system for ablating heart tissue, in accordance with an embodiment of the present invention.

FIG. 1 is a schematic, pictorial illustration of a system 20 for cardiac ablation treatment in a heart 24 of a subject, in accordance with an embodiment of the present invention. System 20 comprises an elongate invasive probe, typically a catheter 22, which is inserted by an operator 23 through a vein or artery of the subject into a chamber of the heart. The catheter comprises, at its distal end, a position sensor, at least one ablation element, such as an ablation electrode, and, typically, one or more additional physiological sensors, as described below with reference to FIG. 2.

Catheter 22 is connected to and controlled by a console 21, which typically comprises a location system control unit 36, an ablation power generator 38 and a sensor monitoring and control unit 34. These elements are connected to the proximal end of catheter 22 via a junction box 32. Junction box 32 routes (a) conducting wires and temperature sensor signals from catheter 22 to ablation power generator 38, (b) position sensor information from the position sensor in catheter 22 to location system control unit 36, and (c) physiological sensor signals from the sensor or sensors in catheter 22 to sensor monitoring and control unit 34. Unit 34 may also be coupled to receive signals from one or more body surface sensors, such as ECG electrodes, so as to provide an ECG synchronization signal to console 21.

A computerized controller 30 receives and analyzes data from sensor monitoring and control unit 34 and location system control unit 36, and also controls ablation power generator 38. Based on the position and orientation coordinates of the catheter, as provided by control unit 36, and the sensor data provided by unit 34, controller 30 generates a graphical representation of heart 24, typically a three-dimensional map 39, on a display 37. The map is used to show the predicted and actual extents of ablation engendered in the tissue of heart 24 by catheter 22, as described hereinbelow.

Figure 2:
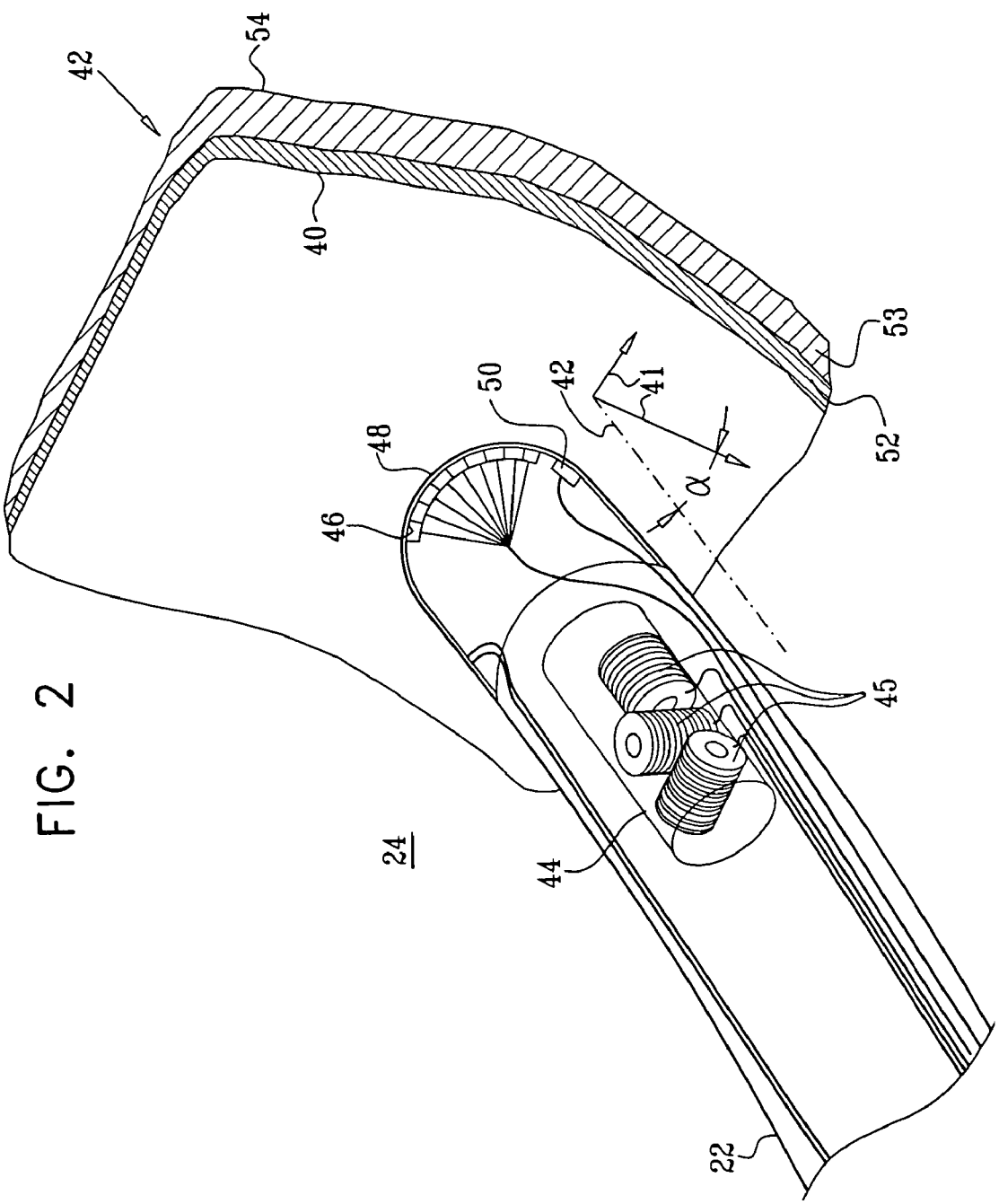
FIG. 2 is a schematic, pictorial illustration showing the distal tip of a catheter in contact with endocardial tissue, in accordance with an embodiment of the present invention.

Location system control unit 36 actuates a set of external radiators 28, which are located in fixed, known positions external to the subject. Radiators 28 generate fields, typically electromagnetic fields, in the vicinity of heart 24. The position sensor in catheter 22 (as shown in FIG. 2) generates signals in response to the fields. The signals are processed by location system control unit 36 in order to determine position and orientation coordinates of the catheter. Alternatively, the fields may be generated by a suitable radiator in the catheter, and detected by external receivers, in place of radiators 28. For some applications, a reference position sensor (not shown) is maintained in a generally fixed position relative to heart 24. The reference sensor may be on a reference patch, attached to the exterior of the body of the subject, for example, or on an internally-placed catheter. By comparing the position of catheter 22 to that of the reference sensor, the coordinates of catheter 22 are accurately determined relative to the heart, irrespective of motion of the subject. Alternatively, any other suitable method may be used to compensate for such motion.

Ablation power generator 38 generates energy, which is applied by catheter 22 to perform ablation of heart tissue. Typically, the ablation power generator generates RF electrical energy for performing RF ablation, as is known in the art. Alternatively or additionally, the ablation power generator may induce ablation by other techniques known in the art, such as laser ablation, cryogenic ablation, ultrasound ablation, radioactivity-induced ablation, or chemically-induced ablation. Ablation power generator 38 typically also measures the energy applied to the tissue of the cardiac chamber by the catheter and the impedance between the catheter and the heart wall, as described below. The ablation power generator conveys this information to controller 30 for processing and analysis.

When a monopolar electrode on catheter 22 is used to ablate the heart tissue, system 20 typically comprises a back-pad electrode 26 to complete the electrical circuit through the subject's body. The back-pad electrode is preferably positioned to be in contact with the skin of the subject's back, adjacent to heart 24, during the procedure. In this case, generator 38 measures the impedance between the catheter tip electrode and back-pad electrode 26. Alternatively, the catheter may comprise bipolar or multipolar electrodes, in which case the contact impedance may be measured between the electrode poles.

Prior to the cardiac ablation procedure, catheter 22 is inserted into the chamber of heart 24, and is used to acquire and record geometric and electrical information about the internal surface of the chamber of the heart. Preferably, position and electrical information is acquired at an easilyidentifiable annotation point in time, such as at the point of diastole, over a number of cardiac cycles. A geometrical and, optionally, electrical map based on this information is generated using mapping techniques known in the art. Exemplary techniques for this purpose are described in U.S. Pat. Nos. 6,226,542 and 6,301,496, in European patent application EP 1 125 549 and the corresponding U.S. patent application Ser. No. 09/506,766, and in U.S. Pat. No. 6,400,981, whose disclosures are incorporated herein by reference. Electrical signals from the catheter electrode(s) may be measured using techniques described in U.S. Pat. No. 6,584,345, whose disclosure is likewise incorporated herein by reference. Alternatively or additionally, an electroanatomical voltage amplitude map may be acquired.

Alternatively or additionally, a cardiac map generated during a previous cardiac catheterization procedure may be used, or a cardiac map may be acquired from another source, such as a map created using an imaging modality, such as fluoroscopy, MRI, echocardiography, CT, single-photon computed tomography (SPECT), or positron emission tomography (PET). Further alternatively, aspects of the present invention may be implemented without the use of a cardiac map.

FIG. 2 is a schematic, pictorial illustration showing a distal portion of catheter 22 in contact with heart tissue 42, in accordance with an embodiment of the present invention. Catheter 22 comprises at least one position/orientation sensor 44 and a tip electrode 48, and optionally comprises one or more ultrasonic transducers 46 and/or a temperature sensor 50. All of these elements are preferably fixed at or near the distal tip of the catheter. Temperature sensor 50 may comprise, for example, a thermocouple and/or a thermistor. Tip electrode 48 is configured to serve as an ablation device, applying electrical signals to tissue 42 for ablating sites of abnormal conduction. Electrode 48 may comprise a sonolucent material, as described, for example, in the above-mentioned U.S. Pat. No. 5,588,432, so as not to interfere with ultrasonic signals transmitted and received by transducers 46. Electrode 48 may also be configured to receive electrical signals for diagnostic purposes, such as mapping of electrical potentials in the heart. Alternatively or additionally, further electrodes (not shown) are provided for mapping and/or other diagnostic purposes. Further alternatively or additionally, the ablation device in catheter 22 may comprise a high-power ultrasonic transducer array, or other means for performing ablation, as are known in the art.

Position/orientation sensor 44 (referred to hereinafter simply as a "position sensor") generates signals that are used to determine the position and orientation of catheter 22 within the chamber of the heart. In the embodiment shown in FIG. 1, sensor 44 comprises one or more sensing coils 45, which act as AC magnetic field receivers, to sense AC magnetic fields generated by radiators 28 (which are also referred to as magnetic field transmitters or field generators). Radiators 28 generate AC magnetic fields to define a fixed frame of reference. In response to the magnetic fields, coils 45 generate signals, which are conveyed by wire to control unit 36 (FIG. 1). The control unit analyzes the signals in order to determine the position and orientation coordinates of the catheter tip. Some of the position sensing and mapping features of catheter 22 and system 20 are implemented in the NOGA-STAR catheter and in the NOG™ and CART™ systems, marketed by Biosense Webster, Inc. Further aspects of the design of catheter 22 and of system 20 generally are described in the above-mentioned U.S. patent application Ser. No. 09/506,766 and in U.S. Pat. No. 5,391,199, whose disclosure is incorporated herein by reference.

Alternatively or additionally, other types of position sensors may be used in place of sensing coils 45. For example, wireless position sensors that may be used for the purposes of the present invention are described in U.S. patent application Ser. Nos. 10/029,473 and 10/029,595 (published respectively as U.S. Patent Application Publications US 2003/0120150 and US 2002/0107445), whose disclosures are incorporated herein by reference. Ultrasonic sensing devices, as are known in the art, may also be used for position sensing. Further alternatively or additionally, catheter 22 may be marked with one or more markers whose positions can be determined from outside of the body. Suitable markers include radio-opaque markers to facilitate fluoroscopic measurements.

Sensor 44 may comprise three sensing coils 45, as shown in FIG. 2, or the sensor may alternatively comprise one, two or more sensor coils, wound on either air cores or a core of material. In the embodiment shown in the figure, coils 45 have mutually orthogonal axes, one of which is conveniently aligned with the longitudinal axis of catheter 22. Unlike prior art position sensors (used for other applications), which contain three coils that are concentrically located, or at least whose axes intercept, the sensor coils in the present embodiment are closely spaced along the longitudinal axis of catheter 22 to reduce the diameter of sensor 44 and thus make the sensors suitable for incorporation into catheter 22 (which may also contain a lumen, not shown, as a working channel within the catheter).

The placement of radiators 28, as well as their size and shape, may vary according to the application of the invention. In system 20, radiators 28 comprise wound annular coils from about 2 to 20 cm in outer diameter (O.D.) and from about 0.5 to 2 cm thick, in a coplanar, triangular arrangement, wherein the centers of the coils are from about 2 to 30 cm apart. Bar-shaped transmitters or even triangular or square-shaped coils could also be useful for such medical applications. In instances in which the subject is prone, as shown in FIG. 1, radiators 28 may be positioned in or below the surface upon which the subject is resting (such as the operating table), below the portion of the subject's body in which the procedure is being performed.

Radiators 28 may be arranged in any convenient position and orientation, so long as they are fixed in respect to some reference frame, and so long as the radiator coils are non-overlapping (i.e., there are no two coils with the same position and orientation). When driven by location system control unit 36, radiators 28 generate a multiplicity of distinguishable AC magnetic fields that form the combined magnetic field sensed by sensing coils 45 in sensor 44. The magnetic fields are distinguishable with regard to the frequency, phase, or both frequency and phase of the signals in the respective magnetic fields. Time multiplexing is also possible.

Sensor 44 in system 20 is used to determine six position and orientation coordinates (X, Y, Z directions and pitch, yaw and roll orientations) of the distal end and distal tip of catheter 22. For this purpose, at least two sensing coils are typically required in the position sensor. In the present embodiment, three sensing coils 45 are used, as described above, to improve the accuracy and reliability of the position measurement. Alternatively, if only a single sensing coil is used, system 20 may be able to determine only five position and orientation coordinates (X, Y, Z directions and pitch and yaw orientations). Specific features and functions of a position tracking system with a single sensing coil (also referred to as a single axis system) are described in commonly-assigned U.S. Pat. No. 6,484,118, whose disclosure is incorporated herein by reference.

In one embodiment of the present invention, each sensing coil 45 has an inner diameter of 0.5 mm and comprises 800 turns of 16 μm diameter to give an overall coil diameter of 1-1.2 mm. The effective capture area of the sensing coil in this case is about 400 mm². It will be understood that these dimensions may vary over a considerable range and are representative only of a typical range in certain embodiments. In particular, the size of the sensing coils can be as small as 0.3 mm (with some loss of sensitivity) or as large as 2 mm or more. The wire diameter of the sensing coils can typically range from 10 to 31 μm, and the number of turns between 300 and 2600, depending on the maximum allowable size and the wire diameter. The effective capture area may advantageously be made as large as feasible, consistent with the overall size requirements. While coils 45 as shown in FIG. 2 are cylindrical, other shapes can also be used. For example a barrel-shaped coil can have more turns than a cylindrical coil for the same diameter of catheter 22. Alternatively, square coils or coils of other shapes may be useful, depending on the geometry of catheter 130.

As noted above, catheter 22 is coupled to console 21 (FIG. 1), which enables the user to observe and regulate the functions of the catheter. Signal processing circuits in location system control unit 36 or in controller 30 typically receive, amplify, filter and digitize signals from catheter 22, including signals generated by position sensor 44. The digitized signals are received and used by controller 30 to compute the position and orientation of the catheter and to generate map 39. Position sensor 44 may also be used to determine both when the catheter is in contact with myocardial tissue 42 and at what angle, based on map 39 and/or on a pre-acquired image or map of the heart made by other means. In the example shown in FIG. 2, catheter 22 is brought into contact with an inner surface 40 of the heart wall at a point at which the surface has a given orientation (according to map 39), as illustrated by axes 41. The orientation of catheter 22, as determined by sensor 44, is such that a longitudinal axis 42 of the catheter forms an angle α relative to surface 40. This position and orientation information is used by console in estimating the expected extent of ablation by a dose of RF energy to be applied by electrode 48, as described further hereinbelow. The information may similarly be applied when ultrasonic energy or other means are used to ablate the tissue.

Ultrasonic transducers 46 are typically arranged in a phased array, aimed in a forward-looking direction along the axis of catheter 22. Typically, the array comprises at least ten transducers, each of which is no more than 0.5 mm across. Sensor control and monitoring unit 34 drives transducers 46 at high frequency, typically in the range of 15-20 MHz. An array of sixteen transducers under these conditions, for example, is capable of producing images (including Doppler images) of tissue 42 with a resolution of about 0.1 mm. The transducers may be used in this manner to determine the thickness and other qualities of tissue 42 prior to ablation, as well as to assess the progress and results of the ablation procedure.

In one embodiment, transducers 46 are used to determine the temperature of tissue 42 as a measure of the extent of ablation, in addition to or instead of temperature measurements that may be made by temperature sensor 50. To determine the temperature, the propagation speed of ultrasonic waves in a surface layer 52 of tissue 42 is assessed, by measuring the round-trip time of the waves that are reflected from the far surface of layer 52 and return to transducers 46. Generally, the propagation speed of the ultrasonic waves increases with tissue temperature. In water, for example, the speed of ultrasonic waves varies by about 2 m/s per degree. Therefore, the temperature increase will be perceived as a thinning of layer 52, relative to underlying layers, as the ultrasonic waves are reflected back to transducers 46 in a shorter span of time. By measuring and comparing the apparent thickness of layer 52 before and after applying RF ablation, the temperature change in the tissue, and hence the extent of the ablation, can be assessed. When transducers 46 emit and receive ultrasonic waves at frequencies in the range of 10-15 MHz, apparent thickness variations on the order of 0.1 mm or less may be detected in this manner, corresponding to temperature variations on the order of a few degrees.

As another example, transducers 46 may be used to observe creation of microbubbles in tissue 42 due to cavitation during ablation. The number of microbubbles typically increases with the tissue temperature. The microbubbles can be most clearly observed by subtracting successive images formed by transducers 46, wherein the orderly increase and decrease in the density of microbubbles over time can be used to distinguish the microbubbles from background noise in the ultrasonic image. The microbubble density thus observed gives a measure of the tissue temperature.

As still a further example, transducers 46 may be used in a Doppler imaging mode to measure the speed of blood flow in a deeper layer 53 of tissue 42. Ablation of overlying layers, such as surface layer 52, is expected to cause blockage of blood vessels within the deeper layer, thus causing changes in the blood flow velocity. The extent of ablation is thus assessed by measuring the change in velocity resulting from the ablation procedure.

Alternatively or additionally, other methods for measuring tissue temperature and assessing the extent of ablated tissue may be used, as are known in the art. For example, catheter 22 may comprise a miniature nuclear magnetic resonance (NMR) sensor, which can be used to map the extent of ablation in the vicinity of the catheter tip.

Figure 3:
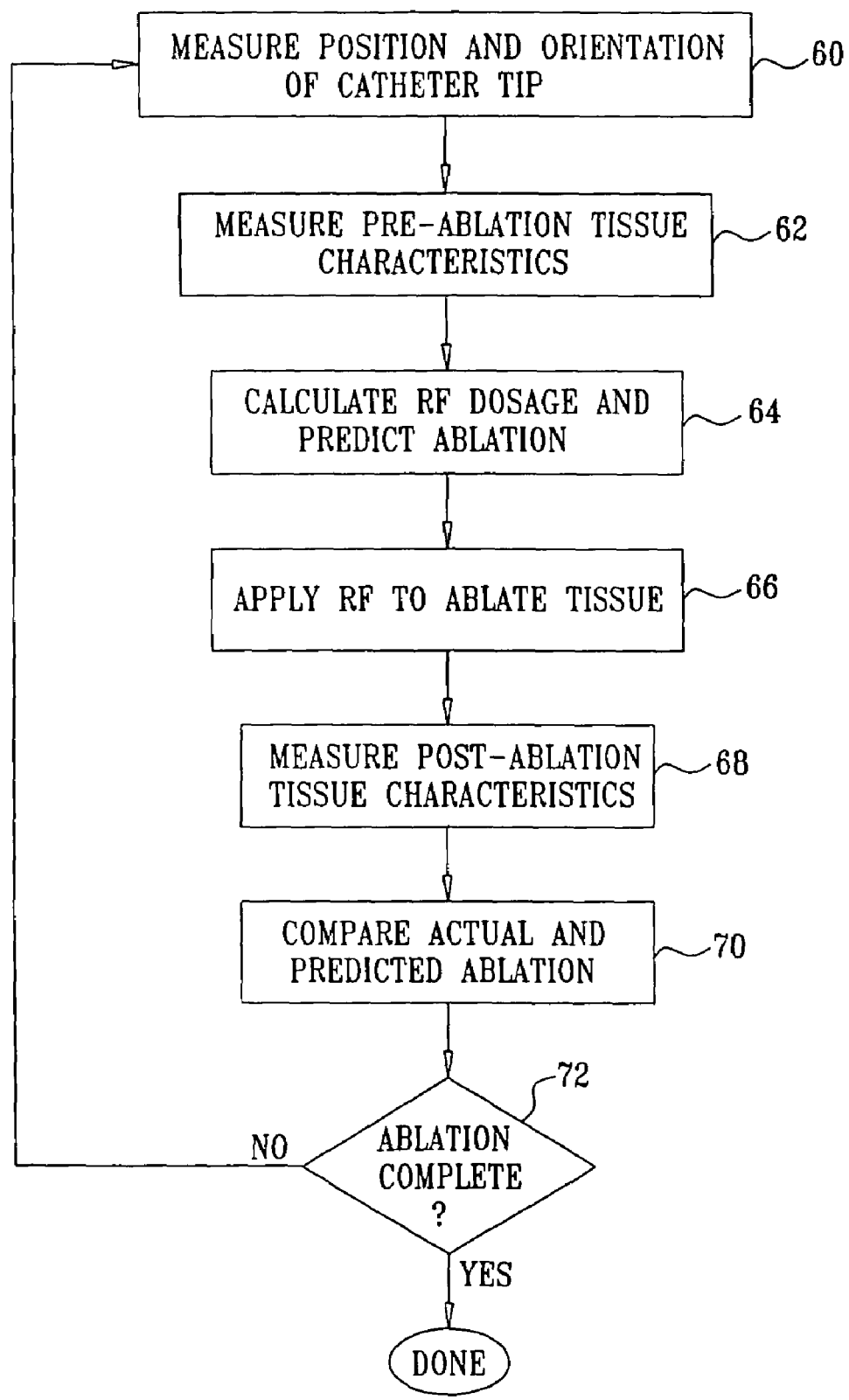
FIG. 3 is a flow chart that schematically illustrates a method for ablating tissue, in accordance with an embodiment of the present invention.

FIG. 3 is a flow chart that schematically illustrates a method for planning and performing an ablation procedure using system 20, in accordance with an embodiment of the present invention. Catheter 22 is brought into contact with inner surface 40 of tissue 42, as shown in FIG. 2, and the position and orientation of the catheter tip are measured using sensor 44, at a catheter positioning step 60. The position and orientation measurements are used in assessing the angle α and penetration depth of the catheter tip relative to surface 40. Operator 23 may manipulate the catheter until it engages tissue 42 at the desired position and orientation.

The sensors in catheter 22 are then used to measure pre-ablation characteristics of tissue 42, at a pre-ablation assessment step 62. For example, ultrasonic transducers 46 may be used to measure the thickness of the heart wall, as given by the distance from the catheter tip to a rear surface 54 of tissue 42. The ultrasonic transducers may also be used to measure blood flow in and around the tissue, using Doppler techniques, and to assess pre-ablation tissue temperature and other qualities, as described above. Additionally or alternatively, the impedance between electrode 48 and back pad 26 (FIG. 1) may be measured in order to determine the quality of the electrical contact between the catheter electrode and tissue 42.

The penetration depth, angle and tissue characteristics are applied by controller 30 in estimating the expected extent of ablation to be expected for a given RF dosage, at a prediction step 64. The controller may use any suitable prediction method known in the art for this purpose, such as a finite element calculation. The expected extent of ablation is typically shown graphically on display 37. Operator 23 may input different RF dosage levels, in which case controller 30 recalculates the expected ablation and updates the display accordingly, enabling the operator to choose the optimal RF dosage. Alternatively, the operator may input desired ablation results, such as the desired depth of ablation (which typically depends on the thickness of tissue 42). In this case, controller 30 determines the RF dosage that will lead to these results. Once the appropriate dosage has been determined, ablation power generator 38 is actuated to apply the RF energy to electrode 48, at a tissue ablation step 66.

After application of the RF energy, catheter 22 measures the ablation that has resulted, at a post-ablation assessment step 68. Measurements made at this stage may include temperature measurements and ultrasonic imaging and/or Doppler measurements, as described above, using transducers 46. Additionally or alternatively, electrode 48 or other electrodes on catheter 22 may be used to measure changes in electrical characteristics, including both tissue impedance and electrophysiological potentials in tissue 42. These measurement results are used by controller 30 is determining the actual extent of ablation that was achieved at step 66.

The actual ablation is compared to the predicted extent of ablation, at a comparison step 70. The comparison may be displayed graphically, on display 37, as shown below in FIG. 4. Additionally or alternatively, controller 30 may use the comparison in order to adjust the prediction parameters that it applies at step 64, so that subsequent predictions (on this patient or other patients) will be closer to the actual results. Based on the measured extent of ablation, operator 23 determines whether the tissue at this site has been ablated to a sufficient temperature and/or depth, at a completion assessment step 72. If so, the operator moves catheter 22 on to the next ablation site or, if the procedure is finished, removes the catheter from the body. On the other hand, if further ablation is required at this site, the procedure described above may be repeated, beginning again from step 60.

Figure 4:
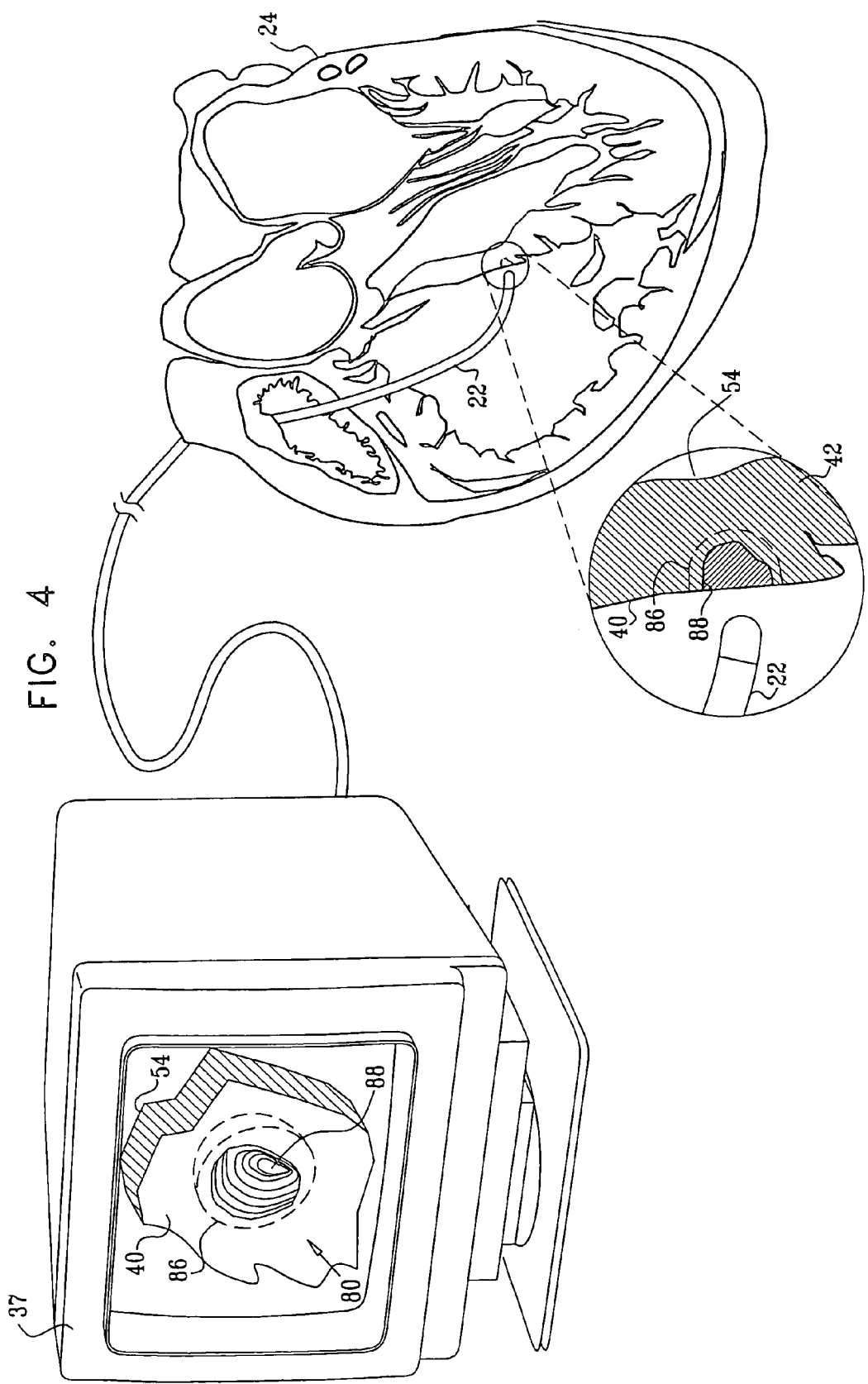
FIG. 4 is a schematic, pictorial illustration showing ablation of heart tissue and a graphical display of predicted and measured results of the ablation, in accordance with an embodiment of the present invention.

FIG. 4 is a schematic, pictorial illustration showing a three-dimensional detail map 80 of an ablation site treated by catheter 22 in heart 24, in accordance with an embodiment of the present invention. The map shows the expected extent of ablation, as calculated at step 64 for a given RF dosage, in the form of a dashed outline 86. The actual ablation zone, as determined at step 68, is shown as a topographical depression 88 in tissue 42. These means of visualization are shown here by way of example, and other visualization methods, typically using color coding, will be apparent to those skilled in the art. On the basis of map 80, operator 23 is able to determine (in the present example) that the actual extent of ablation was smaller than the predicted extent, and that further ablation at this site may be required to make the ablation lesion extend through the entire thickness of tissue 42 to rear surface 54.

Figure 5B:
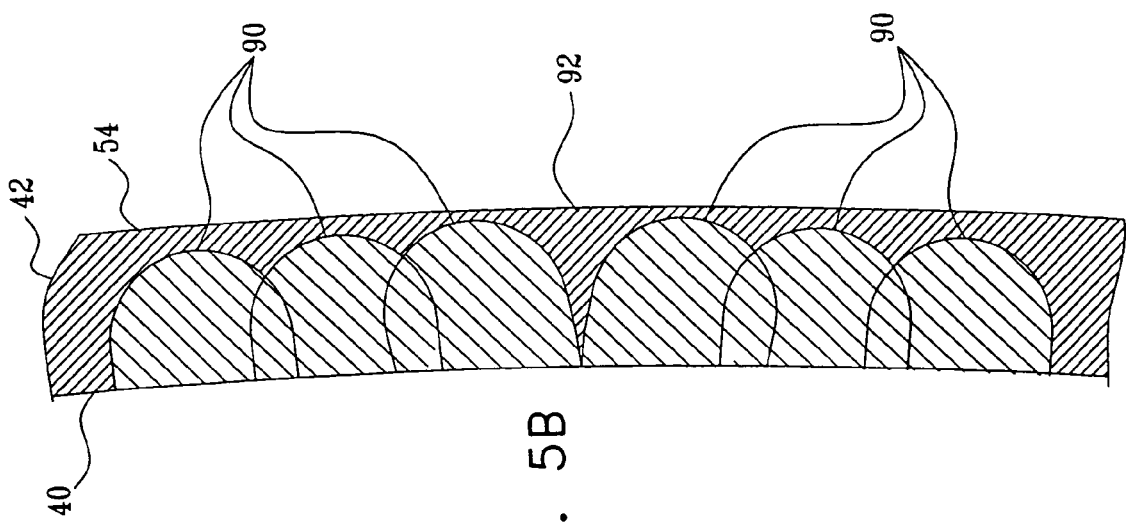
FIGS. 5A and 5B are schematic front and sectional views, respectively, of a row of ablation lesions created by a catheter in heart tissue, in accordance with an embodiment of the present invention.
Figure 5A:
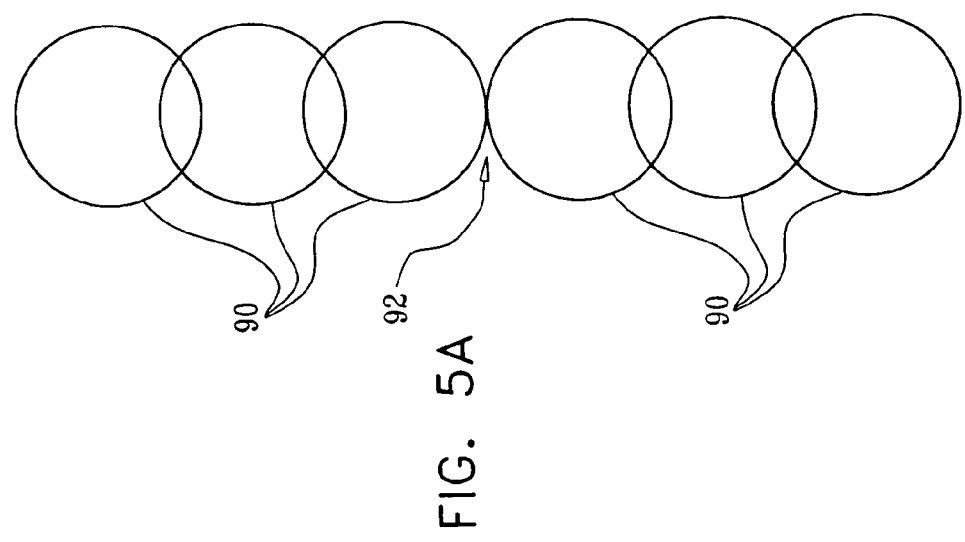

FIGS. 5A and 5B are schematic front and sectional views, respectively, of a row of ablation lesions 90 produced by catheter 22 in heart tissue 42, in accordance with an embodiment of the present invention. Rows and rings of adjacent ablation spots of this sort are commonly used in treating arrhythmias. For example, catheter 22 may be used to ablate sites in a ring so as to isolate the source of an arrhythmia in a pulmonary vein. It is important that lesions 90 penetrate to a sufficient depth in tissue 42, and adequately overlap one another so that all conducting pathways through the line or ring are interrupted. In the example shown in FIG. 5, however, a gap 92 remains within tissue 42 between two of lesions 90. The methods of the present invention, as described above, allow such gaps to be visualized on display 37. Position sensor 44 and transducers 46 then permit the operator to return catheter 22 to the appropriate position and to apply the proper ablation dosage in order to complete the ablation of gap 92.

Although the embodiments described above are directed specifically to RF ablation of cardiac tissue, the principles of the present invention may similarly be applied, as noted above, to other ablation techniques, such as ultrasonic, chemical and cryo-ablation. When ultrasonic ablation is used, the ability provided by embodiments of the present invention to determine the angle of contact between the catheter and the tissue is particularly helpful in determining the angle at which the ultrasonic beam should be aimed into the tissue. Note also that ultrasonic imaging of the tissue, as described hereinabove, may be used advantageously in conjunction with ultrasonic ablation. Furthermore, the methods and apparatus described above may be adapted for use in ablation procedures not only in the heart, but also in other organs of the body, for example, to perform ablation of tumors, particularly (but not exclusively) tumors of the liver, kidney and prostate.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for ablating cardiac tissue in a heart of a subject, comprising:
   a catheter, which is adapted to be inserted into the body and within the heart so as to contact the cardiac tissue to be ablated at a desired position in the heart, the catheter comprising:
   at least one sensor, which measures one or more local parameters at the position prior to and after ablating the tissue and a position sensor which generates signals for determining position and orientation coordinates of the distal end of the catheter; and
   an ablation device, which applies a given dosage of energy to the tissue so as to ablate the tissue;
   a display, which displays a map of the heart; and
   a controller, which determines the position and orientation coordinates of the distal end of the catheter using the signals generated by the position sensor and generates the map showing, based on the one or more local parameters measured by the at least one sensor, a predicted extent of ablation of the tissue to be achieved for the given dosage of energy, and an actual extent of the ablation determined subsequent to ablating the tissue, for comparison with the predicted extent using the position and orientation coordinates.

2. The apparatus according to claim 1, wherein the controller is adapted, responsively to the output of the position sensor, to determine at least one of a penetration depth of the catheter in the cardiac tissue and an orientation angle of the catheter relative to the cardiac tissue, and to predict the extend of the ablation responsively to the at least one of the penetration depth and the orientation angle.

3. The apparatus according to claim 1, wherein the controller is adapted to generate the map by processing the output of the position sensor as the distal end of the catheter is brought into contact with the cardiac tissue at multiple positions inside the heart.

4. The apparatus according to claim 3, wherein the at least one sensor comprises an electrical sensor, which is adapted to measure electrical potentials at the multiple positions, and wherein the controller is adapted to provide an indication of electrical activity on the map, based on the measured electrical potentials.

5. The apparatus according to claim 1, wherein the at least one sensor comprises one or more ultrasonic transducers, which are adapted to transmit ultrasonic waves into the tissue and to generate an output signal responsively to the ultrasonic waves reflected from the tissue.

6. The apparatus according to claim 5, wherein the controller is adapted to measure a propagation speed of the ultrasonic waves in the tissue responsively to the output signal from the one or more ultrasonic transducers, and to estimate a temperature of the tissue based on the propagation speed.

7. The apparatus according to claim 5, wherein the controller is adapted to assess blood flow in the tissue responsively to the output signal from the one or more ultrasonic transducers.

8. The apparatus according to claim 5, wherein the controller is adapted to determine the actual extent of the ablation based on the output signal from the one or more ultrasonic transducers after applying the given dosage of the energy.

9. The apparatus according to claim 1, wherein the controller is adapted to determine an orientation angle of the distal end of the catheter relative to the cardiac tissue, and to predict the extent of the ablation responsively to the orientation angle.

10. The apparatus according to claim 1, wherein the one or more local parameters comprise at least one of a penetration depth of the distal end of the catheter in the cardiac tissue, an electrical impedance between the catheter and the tissue, a temperature of the tissue and a flow of blood associated with the tissue.

11. The apparatus according to claim 1, wherein the controller is adapted to adjust the dosage of the energy responsively to the map.

12. The apparatus according to claim 1, wherein the ablation device comprises an electrode, which is adapted to apply radio frequency (RF) energy to ablate the tissue.

13. The apparatus according to claim 1, wherein the catheter is adapted to ablate a succession of mutually-adjacent sites in the tissue, and wherein the controller is adapted to provide a visual indication of overlap between the sites.

14. Apparatus for ablating cardiac tissue in a heart of a subject, comprising:
a catheter, which is adapted to be inserted into the body and within the heart so as to contact the cardiac tissue to be ablated, the catheter comprising:
a position sensor, which generates an output indicative of a position and orientation of the distal end of the catheter relative to the cardiac tissue with which the catheter is in contact; and
an ablation device, which applies a given dosage of energy to the tissue so as to ablate the tissue;
a display, which displays a map of the heart; and
a controller, which computes position and orientation coordinates of the distal end of the catheter based on the output from the position sensor and, a prediction of an extent of ablation of the tissue to be achieved for the given dosage of energy, so as to enable the dosage to be adjusted responsively to the prediction using the position and orientation coordinates of the distal end of the catheter.

15. The apparatus according to claim 14, wherein the position sensor comprises one or more sensor coils, which are adapted to generate the output indicative of the position and orientation responsively to an externally-applied magnetic field.

16. The apparatus according to claim 14, wherein the controller is adapted to generate a map of the heart by processing the output of the position sensor as the catheter is brought into contact with the cardiac tissue at multiple positions inside the heart, and recording position coordinates of the distal end of the catheter at the multiple positions.

17. The apparatus according to claim 16, wherein the controller is adapted to determine an orientation angle of the distal end of the catheter relative to the cardiac tissue using the map.

18. The apparatus according to claim 17, wherein the controller is adapted to determine a depth of penetration of the catheter into the cardiac tissue, based on the position coordinates of the catheter and on the map, and to predict the extent of the ablation responsively to the depth of penetration and the orientation angle of the catheter.

19. The apparatus according to claim 14, wherein the catheter comprises a sensor, which is adapted to measure at least one local parameter selected from a list of local parameters consisting of an electrical impedance between the catheter and the cardiac tissue, a temperature of the tissue and a flow of blood associated with the tissue, and wherein the controller is adapted to predict the extent of the ablation responsively to the at least one local parameter.

20. The apparatus according to claim 14, wherein the controller is adapted to adjust the dosage of the energy responsively to the map.

21. The apparatus according to claim 14, wherein the ablation device comprises an electrode, which is adapted to apply radio frequency (RF) energy to ablate the tissue.

* * * * *